United States Patent [19]

Salle et al.

[11] 4,118,392
[45] Oct. 3, 1978

[54] DICARBOXYLIC COMPOUNDS AND POLYESTERS DERIVED THEREFROM

[75] Inventors: Robert Salle; Bernard Sillion, both of Grenoble, France

[73] Assignee: Institut Francais du Petrole, France

[21] Appl. No.: 665,170

[22] Filed: Mar. 9, 1976

[30] Foreign Application Priority Data

Mar. 14, 1975 [FR] France .......................... 75 08320
Dec. 24, 1975 [FR] France .......................... 75 39918

[51] Int. Cl.² .................................................. C07D 209/34
[52] U.S. Cl. ....................................... 260/326 N; 528/289
[58] Field of Search ................................... 260/326 N

[56] References Cited

U.S. PATENT DOCUMENTS 3,051,724  8/1962  Bolton et al. ................ 260/326 N
3,461,136  8/1969  Pruckmayr et al. .......... 260/326 N

*Primary Examiner*—Ethel G. Love
*Attorney, Agent, or Firm*—Millen & White

[57] ABSTRACT

New dicarboxylic compounds of the formula:

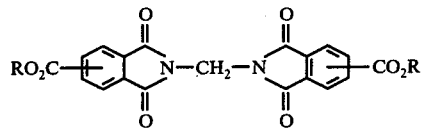

where R is a hydrogen atom or an alkyl, cycloalkyl or aryl group of 1 – 10 carbon atoms, may be used for manufacturing polyester-imides and copolyester-imides — Varnishes obtained therefrom are useful for coating electric metal conductors.

4 Claims, No Drawings

DICARBOXYLIC COMPOUNDS AND POLYESTERS DERIVED THEREFROM

The invention concerns new dicarboxylic acid compounds, their manufacture and their use for manufacturing polyester-imides and copolyester-imides.

The previously disclosed polyester imides are obtained from dicarboxylic compounds which contain in their molecule one or two imide heterocycles and are usually made by condensing one molecule of a biprimary diamine on two molecules of trimellitic anhydride, or by equimolecular reaction of trimellitic anhydride with aminobenzoic acid, or by reacting 2 molecules of aminobenzoic acid with one molecule of a tetracarboxylic acid anhydride; the manufacture of such compounds is disclosed, for example, in the French Pat. Nos. 1,368,741, 1,427,087 and 1,450,704.

The present invention has for object to yield new dicarboxylic compounds comprising two imide heterocycles per molecule; they are manufactured without resort to reactants comprising one or more primary amine groups, whose use is often difficult, injurious and expensive. The dicarboxylic compounds of the invention are of the following general formula:

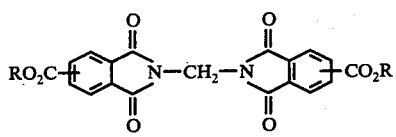
(I)

where R is a hydrogen atom, or an alkyl, cycloalkyl or aryl group of 1-10 carbon atoms.

They can be obtained according to various manufacturing processes.

N,N'-methylene bis trimellitimide may itself be prepared by reacting trimellitic anhydride with hexamethylene tetramine; the reaction may be conducted without solvent at temperatures in the preferred range of 150°-220° C., or at the reflux temperature in various solvents such as, for example, acetic acid or N-methyl pyrrolidone. The reaction may be catalyzed, if desired, by adding strong acids such as, for example, sulfuric acid or phosphoric acid. The structure of the compound is determined by its elemental analysis, its spectral IR and NMR characteristics, its acid number and its molecular weight.

The alkyl or cycloalkyl esters of N,N'-methylene bis trimellitimide may be prepared from the di-acid according to conventional esterification methods; the aryl esters may be prepared, for example, by transesterification of a lower alkyl diester or from the intermediate bis acid chloride.

These dicarboxylic compounds may be usefully employed for manufacturing linear or cross-linked polyester-imides and copolyester-imides.

Those of the first type, corresponding to linear sequenced polyester-imides and copolyester-imides, withstand heat remarkably and may be used in the form of films, fibers and shaped articles. They are obtained from a dicarboxylic component and a di-hydroxy component and are remarkable in that their dicarboxylic component is obtained, in a proportion of 5-100% of the carboxylic acid equivalents, from N,N'-methylene bis trimellitimide or its derivatives, of the formula (I), and, in a proportion of 0-95%, from at least one aromatic dicarboxylic acid or ester of the general formula:

$$ROOCH—Ar—COOR \qquad (II)$$

where R is as hereinbefore defined and Ar is a divalent aromatic radical of 5-20 carbon atoms, some of them being, if desired, O, S and N atoms; these radicals may comprise an aromatic ring or several aromatic rings joined or bound with a direct carbon-carbon bond, or with a divalent atom or group such as

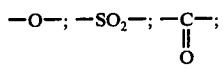

or alkylene of, for example, 1-5 carbon atoms.

Examples of such aromatic dicarboxylic acids are: isophthalic, terephthalic, 4,4'-diphenyl ether dicarboxylic, 4,4'-benzophenone dicarboxylic, naphthalene dicarboxylic acids, either unsubstituted or substituted with halogen atoms or groups inert to the reaction, such as $—NO_2$, $—OCH_3$ or alkyl.

The dihydroxy component is obtained from at least one aliphatic or cycloaliphatic diol of, for example, 2-12 carbon atoms; diols to be used in the invention, either individually or as mixtures, are, for example, ethylene glycol; 2,2-dimethyl 1,3-propane diol; 1,4-butane diol; 1,5-pentane diol; 1,6-hexane diol; 1,10-decane diol; 1,12-dodecane diol; diethylene glycol; 1,4-hexane diol; 1,5-hexane diol; 1,4-pentane diol; 1,4-bis hydroxymethyl cyclohexane; the preferred compounds being the biprimary diols boiling below 300° C.

The invention also concerns the use of polymers of a second type which are heat-resistant, cross-linked polyesterimides and copolyester-imides. They are useful in the form of resins soluble in cresylic acid and cresols for enameling electric metal conductors.

In these resins the carboxylic component is supplied from N,N'-methylene bis trimellitimide of the general formula (I) in a proportion of 5-100% and preferably 10-60% of the carboxylic acid equivalents, and from at least one aromatic dicarboxylic acid of the general formula (II) in a proportion of 0-95% and preferably 40-90% of the carboxylic acid equivalents. The carboxylic component may also be supplied from the corresponding esters.

The polyhydroxy component of the resins of this type is supplied from at least one polyol having at least three hydroxy groups, in a proportion of 50-100% of the hydroxy equivalents, and from at least one aliphatic or cycloaliphatic diol having, for example, 2-10 carbon atoms, in a proportion of 0-50% of the hydroxy equivalents.

Examples of polyols having at least three hydroxy groups are: aliphatic triols, such as glycerol, 1,1,1-trimethylol ethane or 1,1,1-trimethylol propane, aliphatic tetrols, such as pentaerythritol, aliphatic hexols, such as sorbitol or mannitol, or heterocyclic triols, such as tris(-hydroxyethyl) isocyanurate or tris (hydroxypropyl) isocyanurate, the preferred polyol being tris (hydroxyethyl) isocyanurate which is hereinafter referred to as T.H.E.I.C.

Any of the previously mentioned aliphatic and cycloaliphatic diols may be used, although the preferred diol is ethylene glycol.

The manufacture of the sequenced linear polyesterimides and copolyester-imides is preferably carried out by conventional polytransesterification reaction between esters of type (I) where R is preferably a lower alkyl group, such as methyl or ethyl, and the previously mentioned diols, if desired, in the presence of a lower diester of an aromatic dicarboxylic acid of formula (II). The diol is generally used in excess, so that the ratio of the hydroxy equivalents to the carboxy equivalents is preferably higher than or equal to 2.

In a first step, the transesterification reaction is conducted by heating the reactants in an inert atmosphere at a temperature higher than the melting points of the reactants, preferably from 100° to 300° C. During this step, the alcohol of the diester-imide is liberated and is preferably removed from the reaction mixture. In a second step, heating is continued, generally under reduced pressure, preferably below 10 mm Hg, so that the chains of the polymer lengthen by removal of the diol excess.

Any conventional transesterification catalyst employed for preparing polyesters may be used to obtain the polyesterimides of the invention. These catalysts are listed in the article by R.E. WILFONG, Journal of Polymer Science, volume 54, pages 385 to 410, 1961. Among these catalysts, the following are preferably used: the alkyl titanates, such as, for example, butyl titanate associated to manganese or magnesium acetate, litharge associated to antimony trioxide or germanium oxide. The catalyst, or mixture of catalysts, is preferably employed at a concentration of from 0.001% to 0.1% b.w. of the reactants to be used.

The polycondensation time is usually 1 to 6 hours, so that the inherent viscosity of the resulting polyesterimide attains at least about 0.5 dl/g, as determined at 30° C. with a solution at 0.5 g/100 ml in a phenolic solvent.

The obtained linear polyester-imides have softening temperatures usually lower than 260° C., depending on their composition; their glass transition temperatures are very high and some of them may be used at high temperature.

They can be easily shaped by several processes, such as extrusion, and used as sheets, plates, films, fibers or shaped articles according to conventional techniques.

The cross-linked polyester-imides and copolyester-imides of the invention are manufactured according to known methods, preferably by transesterification, using lower (methyl or ethyl) alkyl esters of the diacid-imide of formula (I) and dicarboxy compounds of formula (II), which are reacted with a mixture of polyols as above defined. The reactants are supplied in such proportions that the ratio of the number of hydroxy equivalents to the number of carboxy equivalents is higher than 1, and preferably from 1.1 to 2.

The condensation reaction is carried out advantageously in a single step, at temperatures from 150° to 230° C. (preferably 190° to 220° C.), in the presence of a transesterification catalyst preferably consisting of a tetra-alkyl titanate whose alkyl groups contain 1-6 carbon atoms. It is preferably conducted in solution in a solvent having a boiling point preferably higher than 190° C., such as N-methyl pyrrolidone, cresylic acid, m-cresol or a cresol mixture; the amount of solvent is usually low, the content of dry material being usually from 60 to 90% by weight. The reaction time obviously depends on the selected reactants, their proportions, the catalyst, the solvent and also the temperature. For example, when operating at 190°-220° C., the heating time is usually 6-20 hours. It is preferred, during the reaction, to let the volatile products of the transesterification reaction evolve from the reaction mixture. They can be collected and the determination of their amount permits to follow the progress of the reaction.

The obtained concentrated solutions of resin constitute base varnishes for manufacturing coating compositions, particularly enameling varnishes for electric metal conductors. These base varnishes can be diluted by addition of one of the above solvents or a mixture of several of them. They can also be diluted with aliphatic or aromatic hydrocarbons, or with aromatic hydrocarbon fractions having preferably a boiling point above 100° C. and which are particularly well adapted to this use.

To improve the possibilities of use of the base varnishes, particularly as coatings for electric metal conductors, it is possible to add various ingredients which can react therein, either in the cold, or while heating at, for example, 90°-180° C. for 1-4 hours.

Thus an alkyl titanate, such as hereinbefore defined, may be added to the base varnish, for example, in a proportion of 0.1-10% by weight of the dry material content of the varnish.

A polyisocyanate may also be added to the varnish, for example in a proportion of 1-15% by weight. This polyisocyanate is, for example, a so-called "blocked" tri-isocyanate obtained by trimerisation of 2,4-tolylene diisocyanate, for example, one of those sold under the trade mark "Mondur S", "Desmodur CTS" and "Mondur SH", or a polyisocyanate, such as that sold under the trade mark "Desmodur APS" and which is prepared from trimethylol propane, tolylene-diisocyanate and phenol, or a diisocyanate of the type diisocyanato-diaryl-alkane, for example 4,4'-diisocyanato diphenyl methane, or a polyisocyanato-aryl-alkane having more than 2 reactive groups.

The enameling of the electric metal conductors by means of these varnishes may be carried out according to any conventional technique.

The following examples illustrate the invention in greater detail but are not to be considered as limitative.

EXAMPLE 1

192 g (1 mole) of trimellitic anhydride, 42 g (0.3 mole) of hexamethylene tetramine and 235 ml of crystallizable acetic acid are charged into a 3-neck flask provided with a cooler, an inlet for inert gas, a thermometer and a magnetic stirring device. The stirred mixture is maintained at reflux for 36 hours in an inert atmosphere; it is then cooled to room temperature; the resulting precipitate is filtered, washed with a large amount of dry acetone, then with water and finally with methanol. The precipitate is dried at 100° C. in vacuo, and there is obtained 110 g (yield: 55.8%) of methylene bis-N,N' trimellitimide melting at about 318° C. By recrystallization in acetic acid, the melting point is raised to 322°-324° C.

| Elemental analysis | | % C | % H | % N |
| --- | --- | --- | --- | --- |
| Calculated for $C_{19}H_{10}N_2O_8$ | (394) | 57.87 | 2.55 | 7.10 |
| Found | | 57.78 | 2.88 | 7.16 |

Acid number (determined by direct titration in dimethylsulfoxide)

Calculated: 0.507 group per 100 g Found: 0.50-0.51

IR spectrum — wide band from 3200 to 2300 cm$^{-1}$ ($\nu$ alcohol and acid).

1770 and 1740 cm$^{-1}$ ($\nu$C=O imide), 1690 cm$^{-1}$ ($\nu$C=O acid).

NMR spectrum (60 MH, DMSO d$_6$), δppm: 5.55, s, (2 H); 7.85 to 8.5, m (6H).

Mass spectrometry — molecular peak m/e = 394.

EXAMPLE 2

19.2 g (0.1 mole) of trimellitic anhydride and 3.9 g (0.025 mole) of hexamethylene tetramine are supplied to a reactor provided with an anchor stirrer and an inert gas inlet pipe. The stirred mixture is maintained at 170° C. for 5 hours under inert atmosphere. After cooling, the product is crushed, washed with dry acetone and then with water. 7.49 g (yield: 38%) of methylene bis-N,N' trimellitimide is obtained; its characteristics are identical to those of the product described in example 1.

EXAMPLE 3

The manufacture is the same as in example 1, except that 1 ml sulfuric acid is added. After 5 hours of heating at reflux, the product is treated as explained in example 1; there is obtained 69 g (yield: 35%) of methylene bis-N,N' trimellitimide melting at 321° C.

EXAMPLE 4

600 ml of absolute ethanol saturated with gaseous hydrochloric acid and 10 g (0.025 mole) of methylene bis-N,N' trimellitimide obtained according to example 3 are introduced into a flask provided with a stirrer and a reflux cooler. The mixture is heated at reflux for 5 hours, during which progressive dissolution takes place. The warm solution is filtered; by cooling, there is formed a precipitate which is isolated, washed with ethanol and dried. There is obtained 7.1 g (yield 63%) of ethyl methylene bis-N,N' trimellitate melting at 151°-152° C.

| Elemental analysis | | % C | % H | % N |
|---|---|---|---|---|
| Calculated for C$_{23}$H$_{18}$N$_2$O$_8$ | (450) | 61.33 | 4.03 | 6.22 |
| Found | | 61.30 | 4.08 | 6.55 |

IR spectrum — 1780 and 1740 cm$^{-1}$ ($\nu$ C=O imide), 1725 cm$^{-1}$ ($\nu$C=O ester).

NMR spectrum (60 MH, DMSO d$_6$), δppm = 1.35, t, (6H); 4.35, q, (4H); 5.5, s, (2H); 7.85 to 8.5, m, (6H).

EXAMPLE 5

By proceeding as described in example 4, there is esterified 20 g of methylene bis-N,N' trimellitimide obtained according to example 1 by means of 1 liter of absolute methanol saturated with HCl. After drying, there is obtained 18 g (yield: 84%) of the methyl diester of methylene bis-N,N' trimellitimide melting at 205° C.

| Elemental analysis | | % C | % H | % N |
|---|---|---|---|---|
| Calculated for C$_{21}$H$_{14}$N$_2$O$_8$ | (422) | 59.72 | 3.34 | 6.63 |
| Found | | 59.53 | 3.60 | 7.0 |

IR spectrum — 1780 and 1745 cm$^{-1}$ ($\nu$C=O imide), 1725 cm$^{-1}$ ($\nu$C=O ester).

NMR spectrum (60 MH, DMSO d$_6$), δppm = 3.9, s, (6H); 5.50, s, (2H); 7.82 to 8.45, m, (6H).

EXAMPLE 6

A mixture of 22.5 g (0.05 mole) of the ethyl diester of methylene N,N' bis trimellitimide of example 4, 17.7g (0.15 mole) of 1.6-hexane diol and 5 ml of a catalyst solution prepared by dissolving 2 g of butyl titanate and 0.5 g of manganese acetate into 1000 ml of anhydrous methanol are introduced into a polymerization pipe provided with a mechanical stirrer, an inert gas port and a pipe for discharging the alcohol.

The stirred mixture under argon stream is heated to 250° C. for 30 minutes and maintained for 1 hour at this temperature. The pressure is then progressively reduced and heating is continued under 5.10$^{-2}$ mm Hg for 1 hour at 250° C. and 1 hour at 270° C.

There is obtained a polyester-imide having an inherent viscosity of 0.60 dl/g (determined at 30° C. at a 0.5% concentration in o.chlorophenol). Its softening temperature (determined on the block) is about 145° C.; its glass transition point (determined by differential enthalpic analysis) is about 87° C.

EXAMPLE 7

4.22 g (10$^{-2}$M) of methyl methylene-N,N-' bis trimellitate obtained according to example 5 and 1.86 g (3 × 10$^{-3}$ M) of ethylene glycol are polycondensed in the presence of 1 ml of the catalyst solution described in the foregoing example, in an apparatus identical to that described in example 6, while operating as described in that example. There is obtained a polyester-imide of inherent viscosity 0.45 dl/g (determined at 30° C. at a concentration of 0.5% in o.chlorophenol). Its softening temperature is about 225° C., its transition point about 170° C.

EXAMPLE 8

While proceeding according to the technique of example 6, 18 g (4 × 10$^{-2}$ mole) of ethyl methylene-N,N' bis trimellitate of example 4 is condensed on 21 g (0.12 mole) of 1.10decanediol in the presence of 20 mg of litharge and 3 mg of antimony trioxide.

After 3 hours of heating at 270° C. under vacuum, there is obtained a polymer having an inherent viscosity of 0.65 dl/g (at 30° C., at a concentration of 0.5% in o.chlorophenol).

Softening temperature : about 100° C. Glass transition temperature : 64° C.

EXAMPLE 9

4.5 g (10$^{-2}$ mole) of ethyl methylene bis-N,N' trimellitate prepared according to example 4 and 3.2 g (3 × 10$^{-2}$ mole) of neopentylglycol and polycondensed in the presence of 8 ml of the catalyst described in example 6, by using an apparatus and a process identical to those of example 6. The resulting polymer has an inherent viscosity of 0.5 dl/g ; its softening temperature is about 180° C. and its glass transition temperature about 150° C.

EXAMPLE 10

By using the technique described in example 6, there is prepared a copolymer from 7.77 g (4.10$^{-2}$ mole) of methyl terephthalate, 18.01 g (4.10$^{-2}$ mole) of ethyl methylene N,N'-bis trimellitate and 15.1 g (24.10$^{-2}$ mole) of ethylene glycol, in the presence of 8 ml of the catalyst solution described in example 6.

The inherent viscosity of the resulting copolymer, determined at 30° C. at a 0.5% concentration in o.-chlorophenol, is 0.52 dl/g. Its softening point is about 210° C.

EXAMPLES 11-21

Under conditions identical to those of example 6, there is prepared a polyester-imide and several copolyester-imides by using the reactants stated in table I where ethyl methylene-N,N' bis trimellitate is referred to as MBTE and methyl terephthalate as TM. 5 ml of the catalyst solution described in example 6 has been used in each case.

Table I also reports, for each resulting polymer:
- the inherent viscosity determined at 30° C. in o.-chlorophenol at a concentration of 0.5%
- the softening temperature (Tr) determined on the heating bench, and
- the glass transition temperature (Tg) determined by differential enthalpic analysis.

TABLE I

| Ex No | M.B.T.E. weight (g) | M.B.T.E. Molar proportion (millimole) | TM weight (g) | TM Molar proportion (millimole) | DIOL TYPE | DIOL weight (g) | DIOL Molar proportion (millimole) | CHARACTERISTICS η inh (dl/g) | CHARACTERISTICS Tr (°C) | CHARACTERISTICS Tg (°C) |
|---|---|---|---|---|---|---|---|---|---|---|
| 11 | 9.000 | 20 | — | — | 1,4-Butanediol | 4.500 | 50 | 0.48 | 150 | 130 |
| 12 | 13.520 | 30 | 1.940 | 10 | " | 9.000 | 100 | 0.50 | 130 | 112 |
| 13 | 9.000 | 20 | 3.880 | 20 | " | 9.000 | 100 | 0.61 | 125 | 98 |
| 14 | 4.500 | 10 | 5.820 | 30 | " | 9.000 | 100 | 0.57 | 170 | 76 |
| 15 | 13.520 | 30 | 1.940 | 10 | 1,6-Hexanediol | 11.800 | 100 | 0.55 | 105 | 74 |
| 16 | 13.520 | 30 | 5.820 | 30 | " | 17.700 | 150 | 0.48 | 85 | 59 |
| 17 | 4.500 | 10 | 5.820 | 30 | " | 11.800 | 100 | 0.59 | 75 | 42 |
| 18 | 1.801 | 4 | 6.984 | 36 | " | 11.800 | 100 | 0.62 | 115 | 35 |
| 19 | 13.520 | 30 | 1.940 | 10 | 1,10-Decanediol | 17.400 | 100 | 0.60 | 70 | 40 |
| 20 | 9.000 | 20 | 3.880 | 20 | " | 17.400 | 100 | 0.51 | 60 | 33 |
| 21 | 4.500 | 10 | 5.820 | 30 | " | 17.400 | 100 | 0.53 | 40 | <30 |

EXAMPLE 22

8.40 g (21 × 10⁻³ mole) of methylene bis N,N'-trimellitimide, obtained in example 1, 12.48 g (64 × 10⁻³ mole) of methyl terephthalate, 13.50 g (51.7 × 10⁻³ mole) of tris-hydroxyethyl isocyanurate, 3.15 g (50.9 × 10⁻³ mole) of ethylene glycol, 0.15 g of isopropyl titanate and 4.85 g of m. cresol are introduced into a reactor provided with a high-power mechanical stirrer, a pipe for supplying inert gas and a short distillation column.

The stirred mixture is heated to 220° C. and heating is continued at this temperature for 9 hours. After cooling to 180° C., the content is diluted with 45.7 g of m. cresol and 16.8 g of "Solvesso 100". After homogenization, there is obtained a polyester-imide solution having a kinematic viscosity of 520 cSt at 30° C. The polymer separates by acetone addition. Its inherent viscosity is 0.12 dl/g (at 30° C. in m.cresol, at a concentration of 0.5%).

The solution is flowed to coat a thin copper sheet. The solvents are evaporated at 100° C. for 30 minutes, then the sheet is maintained at 300° C. for 3 minutes; the resulting polymer layer adheres perfectly to the copper sheet; it withstands a 20% lengthening without loosening and crack.

EXAMPLE 23

A mixture of 3.19 g (7.1 × 10⁻³ mole) of ethyl methylene-N,N'-bis trimellitate, 4.16 g (21.5 × 10⁻³ mole) of methyl terephthalate, 4.50 g (17.2 × 10⁻³ mole) of tris hydroxyethyl isocyanurate, 1.05 g (17 × 10⁻³ mole) of ethylene glycol, 0.05 g of butyl titanate and 1.62 g of m.cresol is heated under inert atmosphere in a reactor provided with a stirrer, an inlet pipe for inert gas and a short distillation column.

After 8 hours stirring at 220°-230° C., the temperature is decreased to 150° C., and the content of the reactor is diluted with 5 g of m.cresol and 5.6 g of "Solvesso 100". The resulting solution has a kinematic viscosity of 710 cSt at 30° C.

The product is spread over a copper ribbon and heated, thus yielding an enamel having good adherence to the metal and withstanding a lengthening of 25%.

The concentration of the solutions employed for determining the inherent viscosities given in the above examples (0.5%) is 0.5 g per 100 ml of solvent.

"Solvesso 100" used in examples 22 and 23 is a trade mark for a mixture of aromatic solvents boiling between 158° C. and 171° C.

What is claimed:

1. A dicarboxylic compound of the general formula:

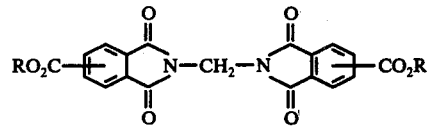

where R is a hydrogen atom or an alkyl, cycloalkyl or aryl group of 1–10 carbon atoms.

2. A dicarboxylic compound according to claim 1, consisting of N,N' methylene bis-trimellitimide.

3. A dicarboxylic compound according to claim 1, consisting of the methyl or ethyl diester of N,N' methylene bis-trimellitimide.

4. A process for manufacturing N,N' methylene bis-trimellitimide of claim 2, which comprises condensing trimellitic anhydride on hexamethylenetetramine.

* * * * *